(12) United States Patent
Hsu

(10) Patent No.: US 10,595,693 B2
(45) Date of Patent: Mar. 24, 2020

(54) DUST COLLECTOR USING FAN HEAT AND DUST COLLECTOR HAVING IRONING FUNCTION

(71) Applicant: Yejen Appliances (Shenzhen) Ltd., Shenzhen (CN)

(72) Inventor: Pei-Cheng Hsu, New Taipei (TW)

(73) Assignee: Yejen Appliances (Shenzhen) Ltd., Shenzhen (CN)

( * ) Notice: Subject to any disclaimer, the term of this patent is extended or adjusted under 35 U.S.C. 154(b) by 164 days.

(21) Appl. No.: 15/742,973

(22) PCT Filed: Jul. 20, 2016

(86) PCT No.: PCT/CN2016/090759
§ 371 (c)(1),
(2) Date: Jan. 9, 2018

(87) PCT Pub. No.: WO2017/016424
PCT Pub. Date: Feb. 2, 2017

(65) Prior Publication Data
US 2018/0228330 A1 Aug. 16, 2018

(30) Foreign Application Priority Data
Jul. 24, 2015 (CN) .......................... 2015 1 0443927

(51) Int. Cl.
*A47L 5/00* (2006.01)
*A47L 9/28* (2006.01)
(Continued)

(52) U.S. Cl.
CPC .................. *A47L 9/28* (2013.01); *A47L 5/00* (2013.01); *A47L 5/24* (2013.01); *A47L 7/0085* (2013.01);
(Continued)

(58) Field of Classification Search
CPC ..................................... A47L 5/00; A47L 5/24
(Continued)

(56) References Cited

U.S. PATENT DOCUMENTS

| 6,964,082 | B2 | 11/2005 | Hsu |
| 8,823,222 | B2 | 9/2014 | Lau et al. |
| 2009/0276974 | A1* | 11/2009 | Khalil ................. H01M 2/1066 15/344 |

FOREIGN PATENT DOCUMENTS

| CN | 201409875 Y | 2/2010 |
| CN | 201929879 U | 8/2011 |

(Continued)

*Primary Examiner* — Robert A Hopkins
(74) *Attorney, Agent, or Firm* — Alan D. Kamrath; Karin L. Williams; Mayer & Williams PC

(57) ABSTRACT

Disclosed is a dust collector using fan heat, comprising a bottom shell (10) and an upper cover (50), wherein a rear end (12) of the bottom shell (10) is provided with an air outlet (122) and a fan assembly (30), the upper cover (50) covers and is connected to the bottom shell (10), air flow from the fan assembly (30) is discharged via the air outlet (122), and the fan assembly (30) is provided with a fan (33) and a stator (331); and the rear end (12) is provided with a lower frame edge (121), the fan assembly (30) and the air outlet (122) are enclosed to form a closed air flow channel (35), and a heat collector (40) is provided on the stator (331) in the air flow channel (35), and can rapidly collect heat and warm the air flow to form hot air flow. Also disclosed is a dust collector having an ironing function, which uses hot air flow to heat an ironing board (60) and then performs ironing and sterilization, so that the dust collector also implements recycling of energy resources while achieving the dust collection effect so as to perform effective sterilization and ironing.

9 Claims, 6 Drawing Sheets

(51) Int. Cl.
*A47L 7/00* (2006.01)
*D06F 75/00* (2006.01)
*A47L 5/24* (2006.01)
*A47L 7/04* (2006.01)
*A47L 9/22* (2006.01)
*A47L 9/10* (2006.01)
*A61L 2/04* (2006.01)

(52) U.S. Cl.
CPC .................. *A47L 7/04* (2013.01); *A47L 9/102* (2013.01); *A47L 9/22* (2013.01); *A61L 2/04* (2013.01); *D06F 75/00* (2013.01)

(58) Field of Classification Search
USPC .................................................... 15/334, 339
See application file for complete search history.

(56) References Cited

FOREIGN PATENT DOCUMENTS

| | | |
|---|---|---|
| CN | 102188190 A | 9/2011 |
| CN | 103948346 A | 7/2014 |
| CN | 204909294 U | 12/2015 |
| EP | 0395787 A1 | 11/1990 |
| JP | H04329916 A | 11/1992 |
| KR | 20130003240 A | 1/2013 |
| WO | WO2013002599 A2 | 1/2013 |

\* cited by examiner

DUST COLLECTOR USING FAN HEAT AND DUST COLLECTOR HAVING IRONING FUNCTION

BACKGROUND OF THE INVENTION

1. Field of the Invention

The present invention relates to the technique of a dust collector and, more particularly, to a dust collector using fan heat and a dust collector having an ironing function.

2. Description of the Related Art

The household vacuum cleaners available currently have been upgraded and provided with either a beater with which dust on quilts, bedclothes and mattresses is vacuumed or a UV lamp with which tiny organisms such as dust mites are sterilized. For effective sterilization, European Publication Number EP0395787B1 discloses a method and apparatus for combating domestic mites, wherein a vacuum cleaner nozzle with a hot air blower from which hot air in the range of 60~70° C. is discharged for killing off dust mites. However, the apparatus which relies on hot air for effective sterilization wastes much energy. Moreover, China Publication Number CN102188190B discloses a vacuum cleaner including a lower shell with a hot plate heated by an electric heater and taken as a flat iron which is used to kill dust mites but still wastes much energy. In addition, the patent of "vacuum cleaner" (Korea Publication Number 10-2013-0003240) based on a flat iron for sterilization discloses a heat exchange plate at the bottom which can absorb heat energy of a fan. However, the heat exchange plate wasting less energy during warm-up receives heat from the fan indirectly but raises limited air flow temperature with which the heat exchange plate is heated insufficiently and incompetent in sterilization. Furthermore, the patent of "motor assembly" (China Publication Number CN102244434A) discloses a heat pipe mounted on a stator for fast cooling. However, the motor's heat energy cannot be reused. In general, the existing techniques depend on hot air flows or a flat iron heated by a direct or indirect heat source such as heater or fan's heat energy to complete sterilization but deserve to be improved by persons skilled in the field.

BRIEF SUMMARY OF THE INVENTION

To overcome the above disadvantages, the present invention provides a dust collector using fan heat which features fast accumulation and removal of heat generated by a running fan and sterilization effect based on hot air flows at an air outlet for annihilation of dust mites and fan cooling effectively. Moreover, a dust collector having an ironing function is provided which heats an ironing board by hot air flows to have an iron effect.

To this end, the present invention presents the technique means as follows:

A dust collector using fan heat includes a bottom shell and an upper cover. A rear end of the bottom shell is provided with an air outlet and a fan assembly. The upper cover covers and is connected to the bottom shell. The fan assembly from which air flows are exhausted to the air outlet is provided with a fan and a stator. The rear end is provided with a lower frame edge, both the fan assembly and the air outlet are encircled for development of an enclosed air flow channel, and a heat collector is provided on the stator in the air flow channel.

Preferably, the fan assembly further includes a front shell and a rear shell, both of which encircle the fan inside. The front shell has an air inlet therein. The rear shell penetrable longitudinally includes an upper frame edge opposite and symmetrical in shape to the lower frame edge for development of an enclosed air circulation space after combination of the upper frame edges and the lower frame edges. The rear shell is further provided with a rear port and a downward exhaust port in an end thereof. The rear port is provided with a rear cover detachably mounted on the rear port. The enclosed air flow channel is formed between the air inlet, the fan and the exhaust port.

Preferably, the rear shell is further provided with a retaining bracket inside by which the fan is fixed. The retaining bracket and the rear shell are connected to each other by four ribbed plates, and any two adjacent ribbed plates develop a flow passage in between for circulation of air flows.

Preferably, the bottom shell is provided with a protuberant shielded area straight opposite to the air outlet such that hot air flows can be retained and whirly circulated inside the shielded area.

Preferably, the heat collector includes an upper shield and a lower shield. The upper shield and the lower shield are combined with each other and fixed on the stator. Each of the upper shield and the lower shield is provided with first fins.

A dust collector having an ironing function includes the above-described dust collector using fan heat, wherein the rear end is provided with a first through-hole in communication with the bottom shell, and an ironing board is provided at the first through-hole and heated by hot air flows blowing the air outlet.

Preferably, a baffle plate is provided between the air outlet and the ironing board. The baffle plate and the lower frame edge surrounding the air outlet develop a gap therebetween such that hot air flows blowing to the ironing board are retained and whirly circulated within the baffle plate and exhausted to outside from the gap to the air outlet.

Preferably, the ironing board is provided with raised second fins opposite to the fan assembly.

The beneficial effects of the present invention are briefly summarized as follows:

1. The heat collector of the dust collector of the present invention is mounted on the stator of the fan and competent in accumulating heat generated by the running fan quickly for removal and reuse of heat via air flows which contribute to less energy waste and fan cooling.

2. Hot air flows are retained and whirly circulated in the protuberant shielded area of the dust collector of the present invention such that temperature is raised for constant supply of heat and sterilization effect.

3. The ironing board of the dust collector of the present invention is heated by hot air flows for sterilization and ironing effects.

LIST OF REFERENCE SIGNS

| 10  | bottom shell       |     |                     |
|-----|--------------------|-----|---------------------|
| 11  | front end          | 12  | rear end            |
| 121 | lower frame edge   | 122 | air outlet          |
| 123 | shielded area      | 124 | first through-hole  |
| 125 | baffle plate       |     |                     |
| 20  | rear frame         |     |                     |
| 30  | fan assembly       |     |                     |
| 31  | front shell        | 311 | air inlet           |
| 32. | rear shell         |     |                     |
| 321 | upper frame edge   | 322 | rear port           |
| 323 | exhaust port       | 324 | retaining bracket   |
| 325 | ribbed plate       | 326 | second through-hole |
| 33  | fan                | 331 | stator              |
| 34  | rear cover         | 35  | air flow channel    |
| 40  | heat collector     |     |                     |
| 41  | upper shield       | 42  | lower shield        |
| 43  | first fin          | 61  | second fin          |
| 50  | upper cover        | 60  | ironing board       |

DETAILED DESCRIPTION OF THE INVENTION

Figure 1:
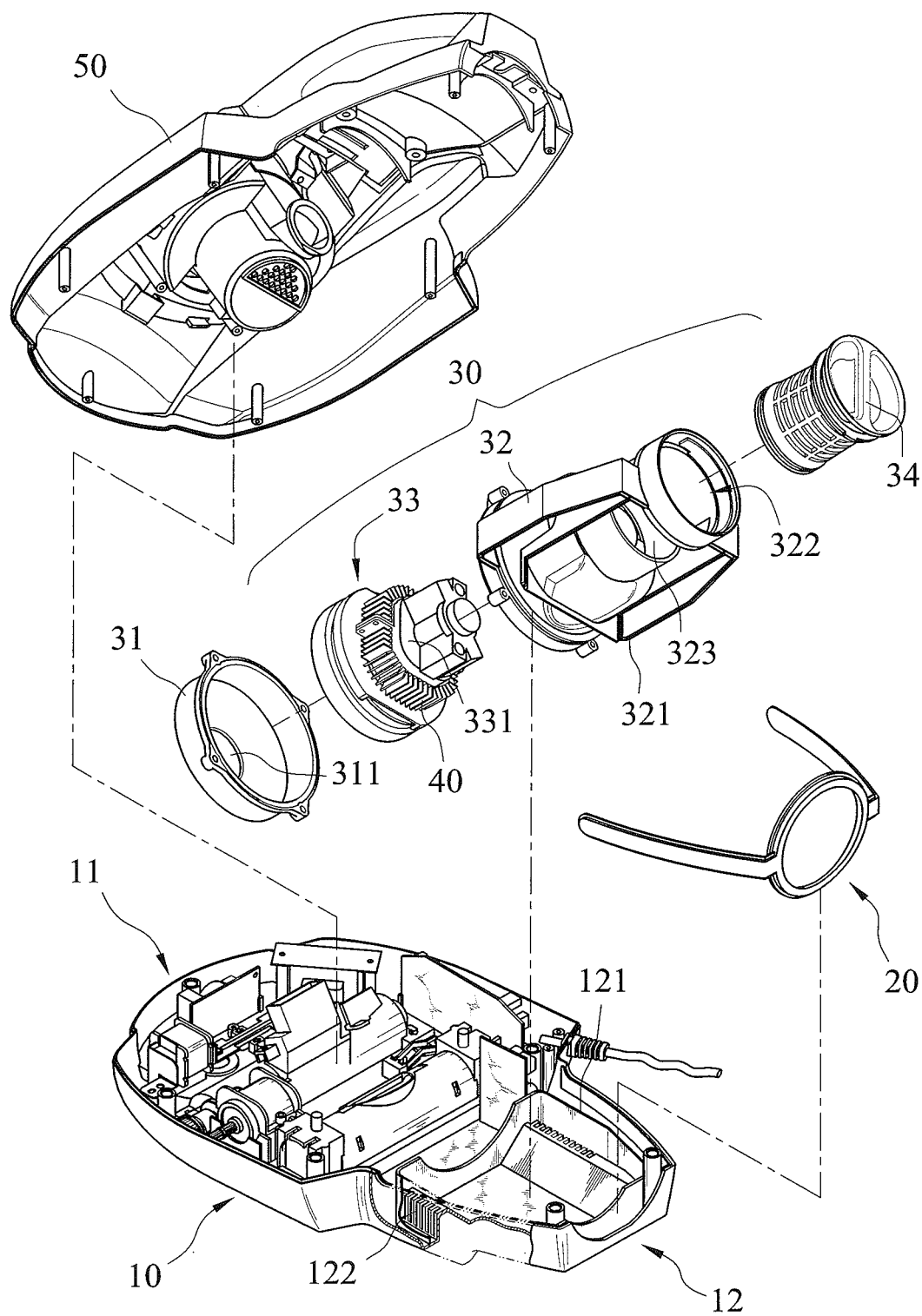
FIG. 1 is an exploded view of a dust collector using fan heat in an embodiment of the present invention.
Figure 2:
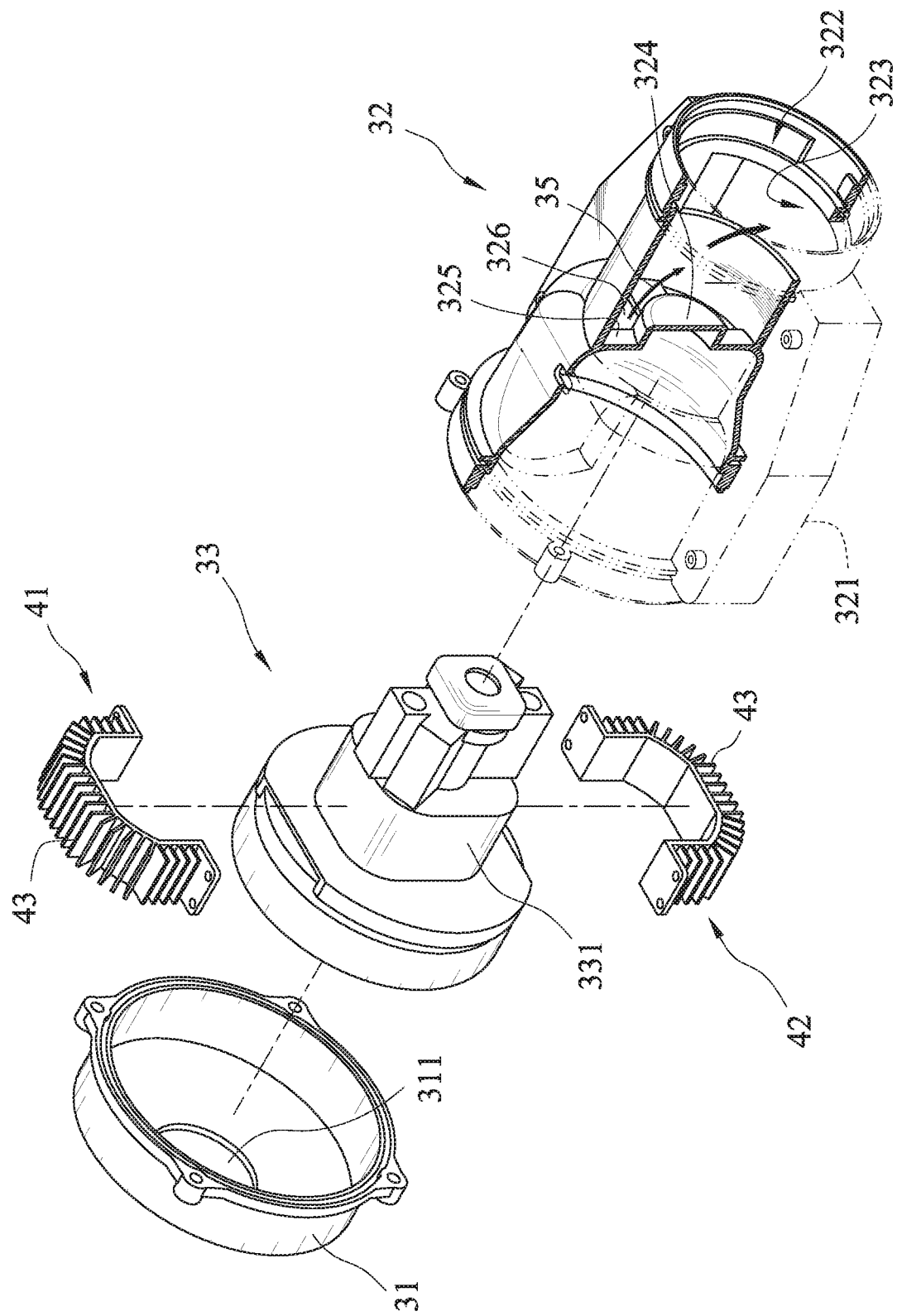
FIG. 2 is an exploded view of a fan and also a schematic view of an air flow channel in the embodiment of the present invention.

Referring to FIGS. 1 and 2, a dust collector using fan heat according to an embodiment of the present invention is shown. A front end 11 of a bottom shell 10 of the dust collector is provided with a beater, a UV lamp, an intake and a dust chamber conventionally. A lower frame edge 121 is formed at a rear end 12 of the bottom shell 10, and an air outlet 122 is opened in the lower frame edge 121 circumferentially and designed as grids. The bottom shell 10 is provided with a protuberant shielded area 123 at the air outlet 122, such that air flows of the air outlet 122 blowing to the shielded area 123 are retained whirly.

The rear end 12 is provided with a rear frame 20 as well as a fan assembly 30 sequentially and also provided with a switch as well as a handle conventionally. An upper cover 50 is combined with the bottom shell 10 for development of an enclosed space around the upper cover 50, the fan assembly 30 and the lower frame edge 121. Air flows of the fan assembly 30 blow to the air outlet 122 restrictively.

The fan assembly 30 is comprised of a front shell 31, a rear shell 32, and a fan 33 encircled by the front shell 31 and the rear shell 32. The front shell 31 is provided with an air inlet 311. The rear shell 32 penetrable longitudinally includes an upper frame edge 321 opposite and symmetrical in shape to the lower frame edge 121 for development of an enclosed air circulation space after combination of the upper frame edges 321 and the lower frame edges 121. The rear shell 32 is further provided with a rear port 322 and a downward exhaust port 323 in an end thereof. The rear port 322 is closed by a detachable rear cover 34 so that air flows in an air flow channel 35 formed between the air inlet 311, the fan 33 and the exhaust port 323 are circulated in the rear shell 32 and guided to the bottom shell 10.

The rear shell 32 is further provided with a retaining bracket 324 inside by which the fan 33 is fixed. The retaining bracket 324 and the rear shell 32 are connected to each other by four ribbed plates 325. Any two adjacent ribbed plates 325 develop a second through-hole 326 in between for circulation of air flows.

The fan 33 is provided with a heat collector 40 which is mounted on a stator 331 thereof and used to accumulate heat generated by the running fan 33 fast. The heat collector 40 is provided just in the air flow channel 35 for quick removal of heat accumulated from the heat collector 40 by circulated air flows and increase in temperature of the circulated air flows. Preferably, the heat collector 40 is made of metal and includes an upper shield 41 and a lower shield 42 for a compact subassembly of the heat collector 40 and the stator 331 assembled or disassembled easily. Furthermore, each of the upper shield 41 and the lower shield 42 includes raised first fins 43 from which heat accumulated is removed by air flows quickly.

Figure 3:
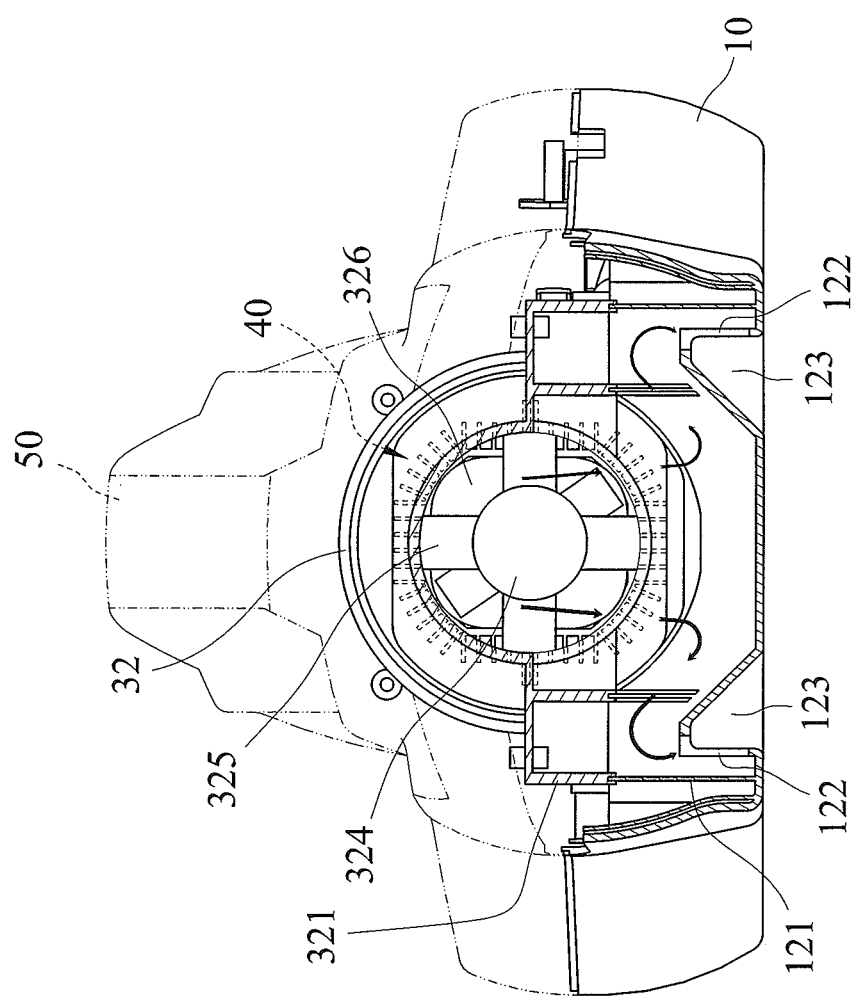
FIG. 3 is a sectional view for an air outlet in a rear end of a bottom shell in the embodiment of the present invention.
Figure 4:
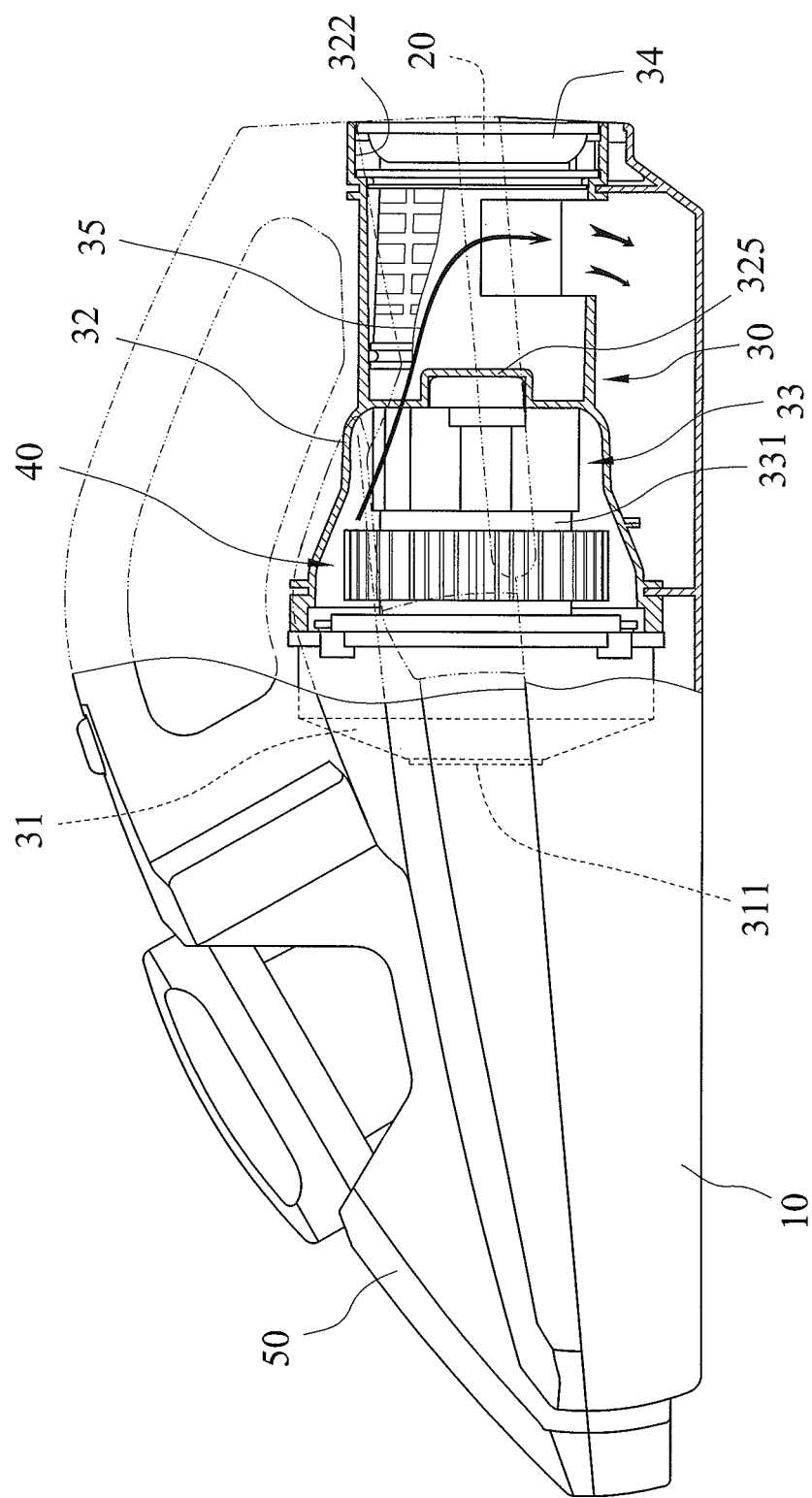
FIG. 4 is an assembled, sectional view of the dust collector in FIG. 1.

Referring to FIGS. 3 and 4, wherein FIG. 3 a sectional view of the grid-shaped air outlet 122 and FIG. 4 is a sectional view of the dust collector with the rear end 12 and the rear shell 32 assembled. Hot air flows passing through the heat collector 40 blow downward from the second through-hole 326 to the exhaust port 323 and arrive at the air outlet 122 via the enclosed space encircled by both the upper frame edges 321 and the lower frame edge 121 for sterilization at the air outlet 122. For better sterilization effect, hot air flows can be retained and whirly circulated inside the shielded area 123 which is raised on the bottom shell 10 and straight opposite to the air outlet 122.

Figure 5:
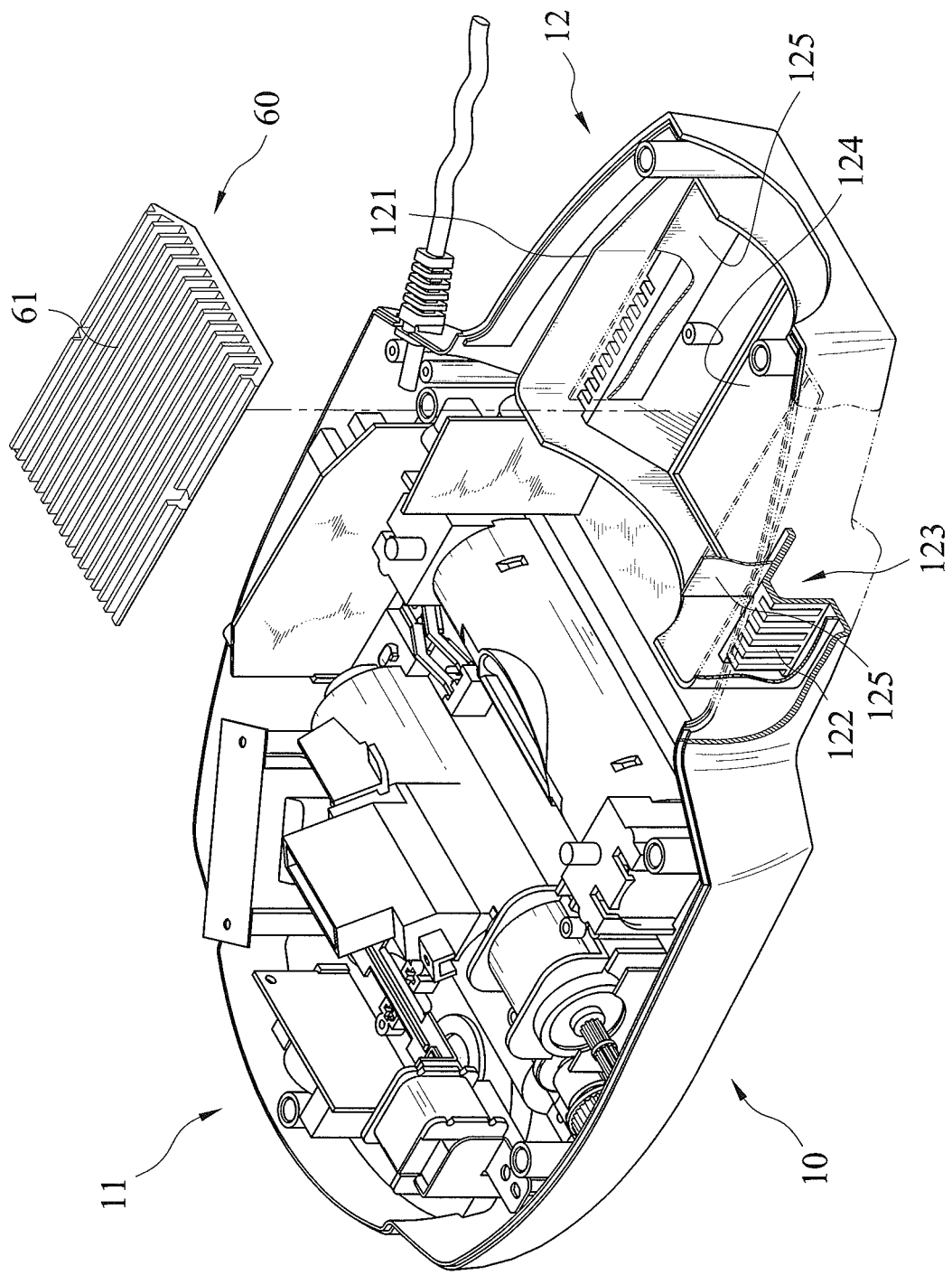
FIG. 5 is a schematic perspective view of a bottom shell of a dust collector having an ironing function in an embodiment of the present invention.
Figure 6:
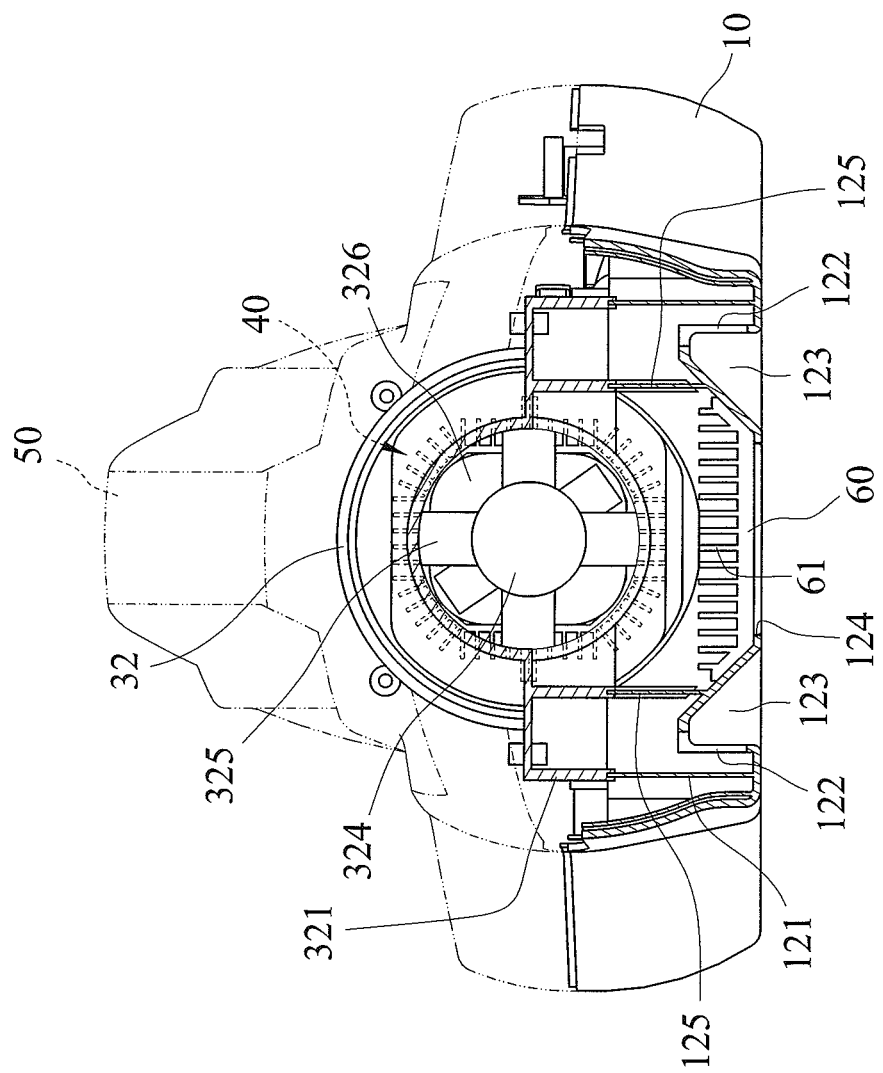
FIG. 6 is a sectional view for the air outlet in the rear end of the bottom shell in FIG. 5.

In order to increase the use of hot air flow, referring to FIGS. 5 and 6, the rear end 12 is provided with a first through-hole 124 in communication with the bottom shell 10, and an ironing board 60 is provided at the first through-hole 124, so that the ironing board 60 can be heated by hot air flows blown down to the air outlet 122. The dust collector being moved on a floor is also a dust collector with an ironing function because the ironing board 60 is capable of ironing vacuumed articles on the floor and killing dust mites along motion paths. For effective accumulation of hot air flows, the ironing board 60 is provided with second fins 61 opposite to the fan assembly 30. Furthermore, a baffle plate 125 is formed between the air outlet 122 and the ironing board 60, and the baffle plate 125 as well as the lower frame edge 121 surrounding the air outlet 122 develop a gap therebetween such that hot air flows blowing the ironing board 60 are retained and whirly circulated within the baffle plate 125, absorbed by the ironing board 60 for increased temperature, and exhausted to outside from the gap to the air outlet 122.

While the invention has been described with reference to the preferred embodiments above, it should be recognized that various modifications and changes, which will be apparent to those skilled in the relevant art, may be made without departing from the spirit and scope of the invention.

The invention claimed is:

1. A dust collector using fan heat, comprising a bottom shell (10) and an upper cover (50), with a rear end (12) of the bottom shell (10) provided with an air outlet (122) and a fan assembly (30), with the upper cover (50) covering and connected to the bottom shell (10), with air flows of the fan assembly (30) exhausted to the air outlet (122), with the fan assembly (30) including a fan (33) and a stator (331); characterized in that the rear end (12) is provided with a lower frame edge (121), both the fan assembly (30) and the air outlet (122) are encircled for development of an enclosed air flow channel (35), and a heat collector (40) is provided on the stator (331) in the air flow channel (35).

2. The dust collector as claimed in claim 1, characterized in that: the fan assembly (30) further includes a front shell (31) and a rear shell (32), both of which encircle the fan (33) inside; the front shell (31) has an air inlet (311) therein; the rear shell (32) penetrable longitudinally includes an upper frame edge (321) opposite and symmetrical in shape to the lower frame edge (121) for development of an enclosed air circulation space after combination of the upper frame edges (321) and the lower frame edges (121); the rear shell (32) is provided with a rear port (322) and a downward exhaust port (323) in an end thereof; the rear port (322) is provided with a rear cover (34) detachably mounted on the rear port (322); the enclosed air flow channel (35) is formed between the air inlet (311), the fan (33) and the exhaust port (323).

3. The dust collector as claimed in claim 2, characterized in that: the rear shell (32) is further provided with a retaining bracket (324) inside by which the fan (33) is fixed; both the retaining bracket (324) and the rear shell (32) are connected to each other by four ribbed plates (325); any two adjacent ribbed plates (325) develop a second through-hole (326) in between for circulation of air flows.

4. The dust collector as claimed in claim 3, characterized in that: the bottom shell (10) is provided with a protuberant shielded area (123) straight opposite to the air outlet (122) such that hot air flows is retained and whirly circulated inside the shielded area (123).

5. The dust collector as claimed in claim 4, characterized in that: the heat collector (40) includes an upper shield (41) and a lower shield (42); the upper shield (41) and the lower shield (42) are combined with each other and fixed on the stator (331); each of the upper shield (41) and the lower shield (42) is provided with first fins (43).

6. The dust collector as claimed in claim 1, characterized in that: the heat collector (40) includes an upper shield (41) and a lower shield (42); the upper shield (41) and the lower shield (42) are combined with each other and fixed on the stator (331); each of the upper shield (41) and the lower shield (42) is provided with first fins (43).

7. A dust collector having an ironing function which comprises the dust collector using fan heat as claimed in claim 4, wherein the rear end (12) is provided with a first through-hole (124) in communication with the bottom shell (10), and an ironing board (60) is provided at the first through-hole (124) and heated by hot air flows blowing the air outlet (122).

8. The dust collector as claimed in claim 7, characterized in that: a baffle plate (125) is provided between the air outlet (122) and the ironing board (60); the baffle plate (125) and the lower frame edge (121) surrounding the air outlet (122) develop a gap therebetween such that hot air flows blowing the ironing board (60) are retained and whirly circulated within the baffle plate (125) and exhausted to outside from the gap to the air outlet (122).

9. The dust collector as claimed in claim 8, characterized in that: the ironing board (60) is provided with raised second fins (61) opposite to the fan assembly (30).

* * * * *